United States Patent [19]
Volkov et al.

[11] 3,941,123
[45] Mar. 2, 1976

[54] APPARATUS FOR JOINT MOVEMENT RESTITUTION

[76] Inventors: Mstislav Vasilievich Volkov, 1 Stroitelnaya ulitsa, 6, korpus 1, kv. 63; Oganes Vardanovich Oganesian, ulitsa Pervomaiskaya, 74, kv. 87, both of Moscow, U.S.S.R.

[22] Filed: May 20, 1975

[21] Appl. No.: 579,066

[52] U.S. Cl. .............................. 128/84 B; 128/92 A
[51] Int. Cl.² ......................................... A61F 5/04
[58] Field of Search .... 128/84 R, 84 A, 84 B, 84 C, 128/92 R, 92 A

[56] References Cited
UNITED STATES PATENTS

| | | | |
|---|---|---|---|
| 2,055,024 | 9/1936 | Bittner, Jr. | 128/92 A |
| 2,120,446 | 6/1938 | Thomas | 128/84 B |
| 2,238,869 | 4/1941 | Haynes | 128/92 A |
| 2,250,417 | 7/1941 | Ettinger | 128/92 A |
| 2,346,346 | 4/1944 | Anderson | 128/92 A |
| 2,406,987 | 9/1946 | Anderson | 128/92 A |

*Primary Examiner*—John D. Yasko
*Attorney, Agent, or Firm*—Steinberg & Blake

[57] ABSTRACT

The proposed apparatus for joint movement restitution comprises two pairs of needles each of which is designed to be driven through one of the joint ends, one of the needles being aligned with the pivotal axis of the joint. Each pair of needles is secured in at least one brace so as to define with the brace a rigid system to be secured on the respective joint end. The two rigid systems are interconnected by distractors which are fixed to one of said systems and connected to the other system by way of ball joints whose fulcrums lie on the longitudinal axis of the needle aligned with the pivotal axis of the joint. The apparatus of the invention provides for joint movement after various angular deformation of the joint ends secured in the apparatus have been corrected.

1 Claim, 4 Drawing Figures

APPARATUS FOR JOINT MOVEMENT RESTITUTION

The present invention relates to medical equipment and, more particularly, to apparatus for joint movement restitution.

The apparatus of this invention may find application in orthopaedics and traumatology for restoring the functions of the elbow-, radio-carpal-, ankle- and interphalangeal joints in cases of contractures, ankyloses and dislocations.

It is known in the art to employ an apparatus for joint movement restitution which comprises two braces carrying plates on each end thereof, said plates being provided with means for tensioning and fixing needles, and a pair of needles is secured in each brace, the brace with the needles secured therein forming a rigid system to be secured on the respective joint end. One brace of the apparatus, which for the sake of convenience is known as an axial brace, serves to fix e.g. the distal end of the humerus by means of an axial needle which is passed through the pivotal axis of the joint and a locking needle which is passed through the joint end through which passes the pivotal axis of the joint. The second brace of the apparatus, termed a rotary brace, fixed the other joint end, e.g. the proximal end of the ulna, with the aid of two needles.

The two rigid systems of needles and braces are interconnected by two distractors each of which is fixed to the rotary brace at one end and connected at the other end to the axial brace by way of a cylindrical hinge whose axis is aligned with the longitudinal axis of the axial needle.

The foregoing known apparatus provides, by means of the needles thereof, the required degree of compression of the joint ends, simultaneously ensuring, by means of the articulated distractors thereof, the required degree of distraction which permits maintaining a gap of constant magnitude between the joint surfaces under both static and dynamic conditions.

The apparatus wherein one brace is capable of turning relative to the other makes it possible to dispense with immobilization while treating diseases and injuries of monocentric joints, permitting of therapeutic movements early in the post-operative period.

Employed in arthroplasty, the apparatus ensures spatial fixation of the joint ends, with the joint surfaces being kept in alignment.

However, the prior art apparatus fails to provide for a desired smoothness of movement in the cylindrical hinges of the apparatus, the reason for which should be sought in the elastic deformation of the apparatus components occurring as the apparatus axts on the joint ends while restituting joint movement, increasing friction in the cylindrical hinges of the apparatus and hampering its functioning. Another disadvantage of the prior art apparatus consists in that movement restitution of the joint fixed in the apparatus is impossible if the joint ends are disposed in angular relationship in the frontal plane of the body.

It is an object of the present invention to provide an apparatus for joint movement restitution which would ensure smooth motion in the articulated joints of the apparatus.

It is another object of the present invention to provide an apparatus for joint movement restitution which would assure active and passive mobility of the joint unloaded by the apparatus, with the joint surfaces being disposed in angular relationship in the frontal plane of the body.

The foregoing objects are attained by the provision of an apparatus for joint movement restitution, comprising two pairs of needles each of which is designed to be driven through one of the joint ends, one of the needles being aligned with the pivotal axis of the joint and each pair of needles being secured in at least one brace in such a way as to form therewith a rigid system to be secured on the respective joint end, and also comprising distractors interconnecting said rigid systems, which distractors are fixed to one of said rigid systems and connected to the other by way of articulated joints, wherein, in accordance with the invention, the articulated joints are formed as ball joints whereof the fulcrums lie on the axis of the needle aligned with the pivotal axis of the joint.

The apparatus of this invention makes for smooth motion in the articulated joints and permits of joint movement after the various angular deformations of the joint ends (e.g. outward bending, inward bending or rotary displacement) have been corrected, with the braces of the apparatus being disposed at a certain angle to each other.

The invention will be further understood from the following description of an exemplary embodiment thereof taken in conjunction with the accompanying drawings, wherein.

As an exemplary embodiment of the invention, discussed hereinbelow is an apparatus for movement restitution of the interphalangeal joints.

Figure 1:
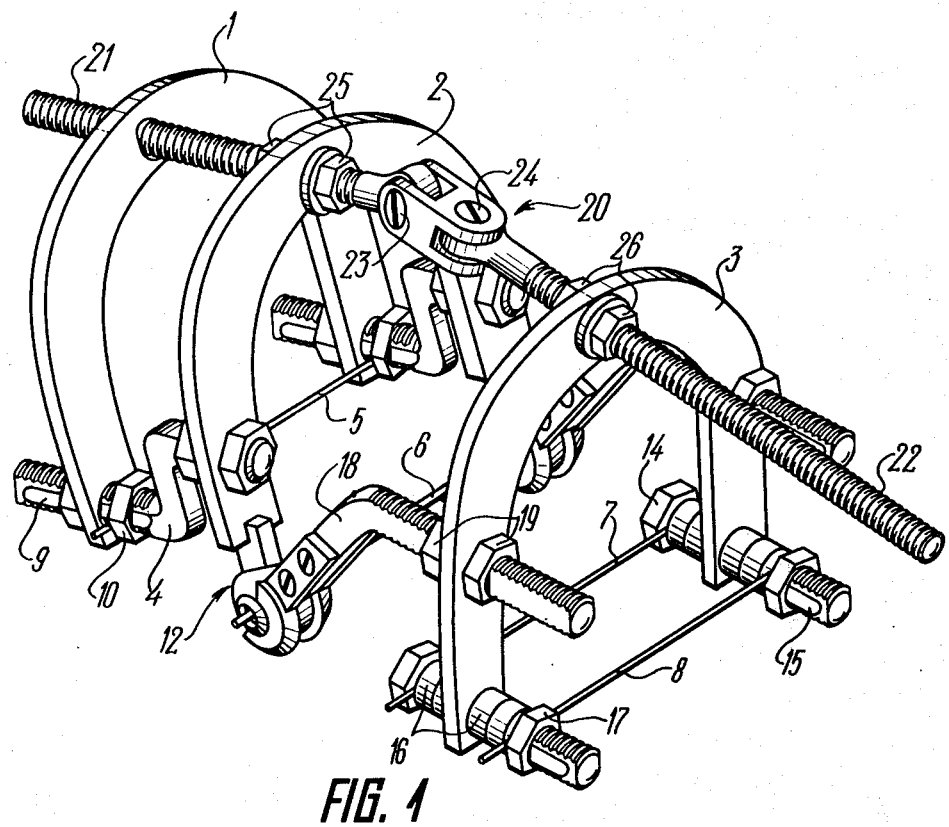
FIG. 1 is a schematic general view of an apparatus for movement restitution of the interphalangeal joints, in accordance with the invention.
Figure 2:
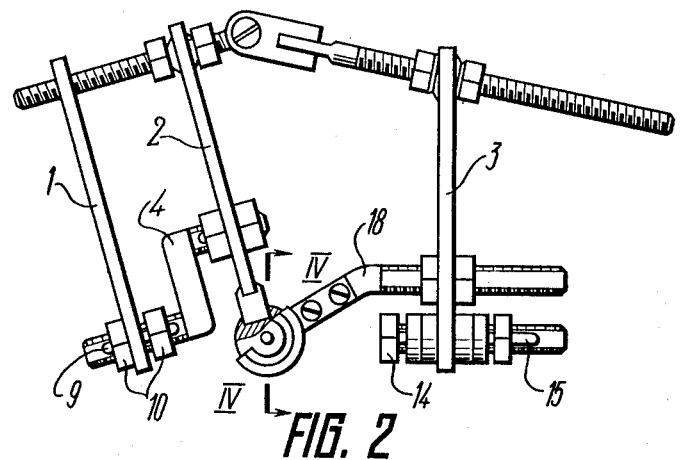
FIG. 2 is a side elevation of the apparatus shown in FIG. 1.

Referring now to the drawings, the apparatus for movement restitution of the interphalangeal joints comprises three braces 1, 2 and 3 (FIG. 1), the braces 1 and 2 being rigidly interconnected by two irregularly shaped fixing bolts 4 (FIGS. 1 and 2).

An axial needle 6 is secured in the brace 2, a locking needle 5 is secured in the brace 1 (FIGS. 1 and 3), and two needles, 7 and 8, are secured in the brace 3.

Figure 4:
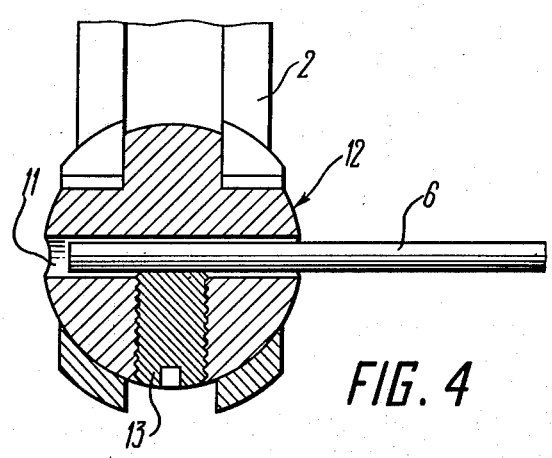
FIG. 4 is a blown-up sectional view taken on the line IV—IV in FIG. 2.

The locking needle 5 passes through notches 9 in the fixing bolts 4 and is secured to the brace 1 with the aid of nuts 10. The axial needle 6 passes through centre holes 11 (FIG. 4) formed in ball joints 12 so fastened to the brace 2 that the fulcrum of the ball joint 12 lies on the longitudinal axis of the needle 6 and is locked by means of clamp screws 13. For fixing the needles 7 and 8 (FIG. 1), the brace 3 is provided with fixing bolts 14, the needles 7 and 8 being passed through notches 15 of the fixing bolts 14. The needles 7 and 8 are pressed against washers 16 fitted over the fixing bolts 14 by means of nuts 17.

The braces 1 and 2 with the needles 5 and 6 form a single rigid system which must be firmly secured, by means of the needle 5 and 6, on the joint end through which passes the pivotal axis of the joint, e.g. for fixing the distal end of the proximal phalanx.

The brace 3 with the needles 7 and 8 forms a second rigid system which is to fix, with the aid of the needles 7 and 8, the other joint end, in this case for fixing the proximal phalanx.

The two rigid systems are interconnected by distractors 18 which are fastened to the brace 2 by means of the ball joint 12 and to the brace 3 by means of two split nuts 19. The split nuts 19 make it possible to vary the length of the distractor 18 between the braces 2 and 3, thereby varying the distance between the fixed needles 5, 6, 7, 8 and the joint ends.

The apparatus is equipped with a detachable bending-unbending arrangement 20 for correcting joint contracture and restituting movement therein. The bending-unbending arrangement 20 comprises two screws 21 and 22 interconnected by articulated joints 23 and 24. One end of the bending-unbending arrangement 20 is secured to the top of the brace 2 by means of split nut 25, while the other end thereof is secured to the top of the brace 3 by means of split nuts 26.

The articulate structure of the distractors 18 of the proposed apparatus ensures that when the apparatus is applied to the interphalangeal joint it does not interfere with the free movements of the adjacent fingers.

The apparatus for joint movement restitution functions as follows.

The apparatus is always applied to the extensor-surface of the limb. This application procedure starts by driving the axial needle through the limb. If the joint surfaces of the elbow-, ankle-, radio-carpal- and interphalangeal joints is damaged, the needle must be aligned with the pivotal axis of the joint end of the bone normally to the main plane of joint rotation through the centre of the humeral pulley, through the centre of rotation of the wrist, and through the centre of the astragalus. The axial needle of the apparatus is passed at a distance from the joint gap equal to the radius of the joint surface: for the elbow joint, this distance is roughly equal to 1.2 cm (i.e., the radius of the capitate eminence pulley); for the ankle joint, 2 cm (astragalus radius); and for the radio-carpal joint, 1.2 cm (radius of wrist bones).

When applying the apparatus after the joint surfaces have been prepared, the axial needle must be aligned with the axis of the bone joint end formed as a semicylinder through which passes the pivotal axis of the joint.

Figure 3:
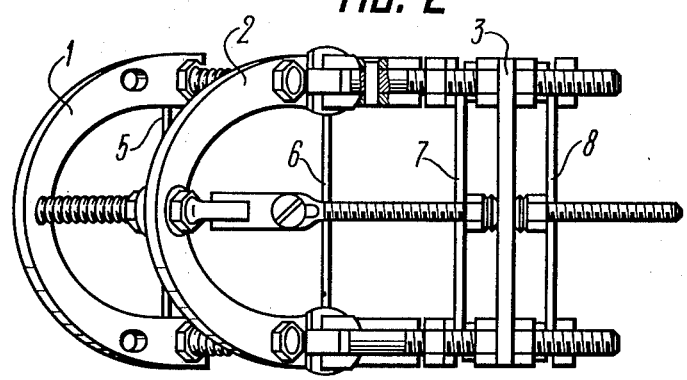
FIG. 3 is a plan view of the apparatus shown in FIG. 1.

Application of the apparatus illustrated in FIGS. 1, 2 and 3 to the interphalangeal joint begins by driving the axial needle 6 e.g. through the distal end of the proximal phalanx, the needle 6 being passed through the centre hole 11 (FIG. 4) of the ball joint 12 and fixed by means of the clamp bolts 13.

Thus, the centre of the ball joint 12 of the apparatus lies on the longitudinal axis of the axial needle 6.

After the axial needle 6 has been put in position, the locking needle 5 (FIG. 1) is driven through the diaphysis of the bone in the frontal plane. Then the other two needles 7 and 8 are driven through the other joint end.

Rotating the split nuts 19 of the distractor 18, the gap between the joint ends is increased. To correct the inward or outward bending of the joint ends, the nuts 19 on the respective side are given a longer travel. Rotating the nuts 26 of the bending-unbending arrangement 20, the brace 3 is turned relative to the braces 1 and 2, causing the joint ends to be flexed and extended.

Since the joint 12 has a ball shape, said turns of the braces are easily accomplished even if the braces 2 and 3 are in angular relationship, which is the case in the course of correction of the outward or inward bending of the joint ends secured in the apparatus.

What is claimed is:

1. An apparatus for joint movement restitution, comprising two pairs of needles each of which is designed to be driven through one of the joint ends, one of said needles being aligned with the pivotal axis of the joint; at least two braces, the tips of said needles of one of said pairs of needles being secured in each of said braces so that said brace together with said needles defines a rigid system to be secured on the respective joint end; two ball joints disposed on both ends of said needle to be aligned with the pivotal axis of the joint, said ball joints being so arranged that the fulcrums thereof lie on the longitudinal axis of said needle; two distractors interconnecting said rigid systems, said distractors being fixed to one of said systems and connected to the other by way of said ball joints.

* * * * *